(12) United States Patent
Fanara et al.

(10) Patent No.: US 6,464,987 B1
(45) Date of Patent: Oct. 15, 2002

(54) PHARMACEUTICAL COMPOSITIONS CAPABLE OF BEING GELLED

(75) Inventors: Domenico Fanara, Wanze (BE); Henri Vranckx, Bruxelles (BE); Michel Deleers, Linkebeek (BE)

(73) Assignee: UCB, S.A., Bruxelles (BE)

( * ) Notice: Subject to any disclaimer, the term of this patent is extended or adjusted under 35 U.S.C. 154(b) by 0 days.

(21) Appl. No.: 09/674,159

(22) PCT Filed: Apr. 16, 1999

(86) PCT No.: PCT/EP99/02551

§ 371 (c)(1),
(2), (4) Date: Oct. 27, 2000

(87) PCT Pub. No.: WO99/56725

PCT Pub. Date: Nov. 11, 1999

(30) Foreign Application Priority Data

Apr. 30, 1998 (BE) ................................................ 9800329

(51) Int. Cl.$^7$ .......................... A61K 9/10; A61K 47/12; A61K 47/24

(52) U.S. Cl. ....................... 424/400; 424/422; 424/425; 424/484; 514/2; 514/784; 514/786; 514/944

(58) Field of Search ................................ 424/400, 405, 424/422, 423, 424, 425, 426, 435, 484; 514/2, 11, 12, 14, 21, 152, 181, 398, 626, 635, 784, 785, 786, 787, 788, 900, 902, 944

(56) References Cited

U.S. PATENT DOCUMENTS

| | | | | |
|---|---|---|---|---|
| 5,230,895 A | * | 7/1993 | Czarnecki et al. | 424/422 |
| 5,230,899 A | * | 7/1993 | Park et al. | 424/450 |
| 5,958,379 A | * | 9/1999 | Regenold et al. | 424/47 |
| 6,117,864 A | * | 9/2000 | Morita et al. | 514/212 |
| 6,210,743 B1 | * | 4/2001 | Clapp et al. | 426/662 |

FOREIGN PATENT DOCUMENTS

| | | |
|---|---|---|
| EP | 0 429 224 | 5/1991 |
| EP | 0 550 960 | 7/1993 |
| WO | 94/10978 | 5/1994 |
| WO | 95/03787 | 2/1995 |
| WO | 97/15285 | 5/1997 |

OTHER PUBLICATIONS

Budavari et al, eds. The Merck Index, 11$^{th}$ ed, Rahway: Merck & Co., Inc. p. 311, 1989.*

* cited by examiner

Primary Examiner—Jeffrey E. Russel
(74) Attorney, Agent, or Firm—Wenderoth, Lind & Ponack, L.L.P.

(57) ABSTRACT

A fluid pharmaceutical composition is described which allows the controlled release of at least one active substance. The composition comprises a therapeutically effective amount of at least one active substance, from 3 to 55% by weight of phospholipid, from 16 to 72% by weight of pharmaceutically acceptable solvent, and from 4 to 52% by weight of fatty acid. The composition has a property of gelling instantaneously in the presence of an aqueous phase.

18 Claims, No Drawings

PHARMACEUTICAL COMPOSITIONS CAPABLE OF BEING GELLED

This application is a 371 of PCT/EP99/02551 filed Apr. 16, 1999.

The present invention relates to pharmaceutical compositions which allow the sustained release of at least one active substance, to methods for preparing these compositions, as well as to their use for administering medicinal products subcutaneously and/or intramuscularly.

The two main extravascular routes of parenteral administration are the subcutaneous and intramuscular routes. Compared to intravenous injection, these two routes of administration for the same aqueous solution of active principle generally produce a slightly delayed and slightly prolonged effect. The bioavailability of the medicinal product is also generally poorer because of a slower absorption, or binding or degradation of the medicinal product at the injection site or in the tissues traversed. Thus, TRH (thyrotropin releasing hormone, a tripeptide) has a bioavailability in mice of 67.5% after subcutaneous administration, and of 31.4% after intramuscular administration (Redding T. W. and Schally A. V., Life Sci., 12, 23 (1970)).

In order to improve bioavailability and to obtain veritable sustained-release preparations, various experimental forms have been developed.

Thus, the encapsulation by liposomes of P-18, which is a peptide with a molecular weight lower than 5000 Dalton, shows that, after intramuscular injection, the peptide remains at the injection site for 7 days (Crommelin D. J. A. and Storm G., Int. Pharm. J., 1, 179 (1987)).

Another means of sustaining the release of an active principle consists of its incorporation into an implant. These implants can be prepared from biodegradable or non-biodegradable polymers. The drawback of this form is linked to its method of subcutaneous introduction by incision or with the aid of a trocar. In addition, if a non-biodegradable polymer is used, the implant must be withdrawn by incision after diffusion of all of the active principle out of the polymer matrix. These systems have been widely developed for the administration of hormones such as LHRH (luteinizing hormone releasing hormone) and its synthetic analogues. Thus, gosereline administered in humans in the form of PLA-GA (copolymer of lactic acid and of glycolic acid) implants allows a very significant and lasting decrease in the level of testosterone in the blood to be obtained (Vogelzang N. J., Chodak G. W., Soloway M. S., Block N. L., Schellhammer P. F., Smith J. A., Caplan R. J. and Kennealey G. T., Urology, 46, 220 (1995)).

Other polymer supports can also be used: micro- or nanoparticles. In this case, only biodegradable polymers are used. In comparison to implants, these particles can be injected with the aid of a conventional syringe, but have the drawback of not being able to be withdrawn from the body in the event of a problem. A very significant and lasting decrease in the level of testosterone was also observed in humans after administration of PLA-GA microparticles containing nafarelin.

These various administration systems have the drawback of sophisticated and complex preparation which requires specific installations.

The applicant has now just discovered novel pharmaceutical compositions which are obtained by an extremely simple preparation method, and which allow sustained release of an active principle. These compositions have the property of gelling instantaneously in the presence of an aqueous phase. They can thus be judiciously used to obtain, via the subcutaneous and intramuscular routes, sustained and programmed release of medicinal products. Upon contact with mucous membranes, a gel forms under the skin or in the muscle, and the medicinal product may diffuse and be released from the gel.

Lipid compositions which undergo a phase transformation upon contact with water have already been presented in the literature.

European patent application 550960 describes compositions for topical application which are intended to prevent perspiration, comprising an antiperspirant which comprises at least one amphiphilic substance, this antiperspirant being capable of forming, in water, an insoluble liquid crystal phase with a periodicity greater than 1. In particular, Example 14 illustrates a composition which is capable of forming an inverted hexagonal crystalline phase upon contact with perspiration, and which is composed of 34 to 50% of oleic acid and of 50 to 66% of lecithin (phosphatidylcholine).

International patent application WO 94/10978 describes emulsifying compositions which are intended to replace the synthetic emulsifiers commonly used in the food, cosmetics, toiletry or pharmaceutical industry. These compositions comprise at least one membrane lipid (phospholipid), at least one natural amphiphile which is not a primary emulsifier ($C_{12}$ to $C_{22}$ fatty acid or fatty alcohol, or combination of a fatty acid and of a fatty alcohol) and, optionally, a hydrophilic medium (aliphatic alcohol such as propylene glycol). These compositions have the property of forming creams (oil-in-water emulsion) with oils or oily substances, and are capable of forming stable emulsions or creams when they are mixed with liposomes.

More particularly, Example 4 describes a composition consisting of 15% by weight of hydrogenated soy bean lecithin (phospholipid), 15% by weight of fatty acid, 45% by weight of fatty alcohol and 25% by weight of alcohol (10% of ethanol and 15% of glycerol). This composition is in the form of a soft waxy mass.

The literature also mentions fluid pharmaceutical compositions intended for treating peridontitis which are in the form of more or less viscous emulsions or suspensions, and which are administered into the periodontal pocket generally with the aid of syringes.

International patent application WO 95/34287 describes biodegradable lipid compositions in the form of L2 crystalline phases which allow the controlled release of active substances and which comprise, besides the active substance, at least one unsaturated fatty acid diacylglycerol which has 16 to 22 carbon atoms or saturated fatty acid diacylglycerol which has 14 to 22 carbon atoms, at least one phospholipid chosen from glycerophosphatides and sphingophosphatides, and, optionally, at least one polar liquid chosen from water, glycerol, ethylene glycol and propylene glycol. These compositions have the characteristic of transforming into cubic liquid crystal phases upon contact with water, which makes it possible to "mould" the active substance in the site where it is desired for the action to take place. The said document mentions, among other uses, the possibility of using such compositions for treating periodontitis. However, the effectiveness of such compositions in the treatment of periodontitis is not illustrated in that document.

European patent 429224 describes compositions which are in the form of gels containing from 1 to 99% by weight of monoolein and from 1 to 90% by weight of active substance, which are placed in the periodontal cavity. In the presence of the surrounding water, these compositions become more viscous and keep the active substance close to its site of action. The active substance is released slowly in controlled fashion.

U.S. Pat. No. 5,230,895 describes the use of compositions which are in the form of solutions or pastes which are capable of transforming into gel when they have been placed in the periodontal pocket. These compositions are biodegradable and allow the controlled release of the active substance in the site of action. They contain a mixture of glycerides and of an active substance chosen such that it is capable of forming a gel in the environment of the periodontal pocket. The compositions illustrated in the said document contain at least 70% of Myverol™ 18-92, which is a composition of sunflower monoglycerides which has a monoglyceride content of at least 90%.

U.S. Pat. No. 5,143,934 describes compositions which allow the administration, by controlled release, of an active substance in a periodontal pocket, and which comprise at least one monoglyceride and at least one plant oil in proportions which are sufficient to form a liquid crystal phase upon contact with the water present in the periodontal pocket. These compositions are solid at room temperature, but they have a melting point which is lower than body temperature.

The present invention relates to fluid pharmaceutical compositions which allow the controlled release of at least one active substance and which comprise a) a therapeutically effective amount of at least one active substance, b) from 3 to 55% by weight of phospholipid, c) from 16 to 72% by weight of pharmaceutically acceptable solvent, and d) from 4 to 52% by weight of fatty acid, these compositions having the property of gelling instantaneously in the presence of an aqueous phase.

According to another aspect, the invention relates to methods for preparing these compositions.

According to a third aspect, the invention relates to the use of these compositions for the controlled release of one or more active substances by subcutaneous and/or intramuscular injection.

The compositions according to the present invention comprise a therapeutically effective amount of at least one active substance. The latter can be lipid-soluble or water-soluble. By way of example, mention will be made of antibiotics, in particular antibiotics which are active against anaerobic bacteria, such as doxycycline or minocycline, and the pharmaceutically acceptable salts thereof, anti-infectious agents such as metronidazole, chlorhexidine, benzalkonium chloride, p-chloro-m-cresol, 2,4-dichlorobenzyl alcohol, hexamidine or chlorofen, and the pharmaceutically acceptable salts thereof, local anesthetics such as lidocaine, procaine, tetracaine, articaine, bupivacaine, mepivacaine or prilocaine, and the pharmaceutically acceptable salts thereof, steroidal or other anti-inflammatory agents such as hydrocortisone, cortisone, prednisone, prednisolone, methylprednisolone; triamcinolone, betamethasone or dexamethasone, and the pharmaceutically acceptable salts thereof, as well as aceclofenac, diclofenac, ibuprofen and piroxicam, and the pharmaceutically acceptable salts thereof, anti-mycotic agents such as griseofulvin, amphotericin B, natamycin or nystatin, and the pharmaceutically acceptable salts thereof, or alternatively peptide active substances such as calcitonin, somatostatin, insulin, bone growth hormone and other growth or repair factors.

The compositions according to the present invention contain from 3 to 55% of phospholipid. The phospholipids which can be used according to the present invention are phosphoric esters of polyols and of fatty acids. They may originate from very varied sources, both natural and via a synthetic pathway. The phospholipids may be hydrogenated or nonhydrogenated. By way of examples, mention will be made of phosphatidylchloine, hydrogenated phosphatidylcholine, phosphatidylglycerol salts, dicaproylphosphatidylcholine or distearoylphosphatidylglycerol salts. These phospholipids can also be used as a mixture. Preferably, the phospholipid which is present in the compositions according to the present invention is phosphatidylcholine.

When the phospholipid is chosen from phosphatidylcholine, phosphatidylglycerol salts, dicaproylphosphatidylcholine or distearoylphosphatidylglycerol salts, the preferred compositions according to the present invention contain from 15 to 55% by weight of phospholipid. When the phospholipid is a hydrogenated phosphatidylcholine, the compositions according to the present invention contain from 3 to 11%, preferably from 3 to 10%, by weight of phospholipid.

The compositions according to the present invention contain one or more pharmaceutically acceptable solvents. The expression "pharmaceutically acceptable solvent" is intended to mean a solvent such as propylene glycol, polyethylene glycols, mineral oils, such as liquid paraffin or silicone oils, or any other solvent in which the phospholipid used is soluble. Mixtures of several pharmaceutically acceptable solvents can also be used. Propylene glycol is preferably used. The solvent used is pharmaceutically acceptable, which means that the solvent will not produce any biological reaction reflected by infections, inflammations or other phenomena of rejection.

The compositions according to the present invention also contain from 4 to 52% of at least one fatty acid. The fatty acids which can be used according to the present invention are saturated or unsaturated organic carboxylic acids containing from 4 to 22 carbon atoms, preferably from 8 to 18 carbon atoms. By way of example, mention will be made of oleic acid, caprylic acid, capric acid, caproic acid, myristic acid, butyric acid, etc. Mixtures of fatty acids can also be used. The preferred fatty acid according to the present invention is oleic acid.

Optionally, the compositions according to the present invention can also contain up to 15% by weight of water. It will be noted that the amount of water which is present in the compositions according to the invention is chosen such that the composition has the desired consistency for the use envisaged.

The applicant has also discovered that phospholipids which are in the form of commercially available mixtures are suitable for the compositions according to the present invention. As examples of such commercially available compositions, mention will be made of Phosal 50 PG™ (55.8% of phosphatidylcholine, 1.9% of soybean fatty acids, 2.9% of sunflower monoglycerides, 1.9% of ethanol, 37.3% of propylene glycol and 0.2% of ascorbyl palmitate) and Phosal 53 MCT™ (60.8% of phosphatidylcholine, 2% oleic acid, 3% of sunflower monoglycerides, 5% of ethanol, 29% of triglycerides and 0.2% of ascorbyl palmitate), which are available from Nattermann Phospholipid GmbH.

The compositions according to the present invention can also contain the following optional components: up to 5% by weight of monoglyceride or of diglyceride or of a mixture of mono- and of diglyceride, and/or up to 15% by weight of triglycerides.

The compositions according to the present invention can also contain one or more preservatives (such as ethanol), one or more antioxidants (such as ascorbyl palmitate) or one or more complexing agents (such as EDTA (ethylenediaminetetraacetate)).

The compositions according to the present invention allow the controlled release of at least one active substance. The term "controlled release" is intended to mean an active substance release profile which is desirable for the treatment envisaged. The release of the active substance can thus be more or less held back or slowed down as a function of the active substance used and of the desired therapeutic effect. It will be noted that the release of the active substance can be easily controlled by simple variations in the proportions of the components of the compositions according to the present invention. The compositions are thus very well suited to diverse therapeutic applications in which the controlled release of an active substance is sought in a very precise biological site.

The compositions according to the present invention are fluid pharmaceutical compositions which are in the form of emulsions, suspensions or oily preparations. They have the property of gelling instantaneously in the presence of an aqueous phase. Specifically, when the compositions according to the present invention are placed in the presence of an excess of aqueous phase, they go from a fluid state to the state of a gel which is immiscible with the surrounding aqueous phase.

According to another aspect, the present invention relates to methods for preparing compositions according to the present invention. The compositions according to the present invention are obtained by a method comprising the following successive steps:

i) the phospholipid(s) is (are) dissolved in the pharmaceutically acceptable solvent(s);

ii) the fatty acid(s) is (are) added to the phospholipid solution with stirring;

iii) the active substance(s) is (are) incorporated into the mixture obtained at the end of step ii), and iv) water is optionally added to the composition obtained in step iii).

When the active substance is water-soluble, it is dissolved in a minimal amount of water before the incorporation in step iii). When the active substance is not soluble in water, it is incorporated in step iii) in the mixture of phospholipid, pharmaceutically acceptable solvent and fatty acid. In the case of substance which is both insoluble in water and insoluble or relatively insoluble in lipid, it is also incorporated in step iii), optionally in micronized form.

The following examples illustrate the present invention without, however, limiting it. In these examples, all the parts are expressed by weight. The following commercially available products were obtained from Nattermann Phospholipid GmbH and have the following compositions (percentages by weight):

Phospholipon 90™ phosphatidylcholine;

Phosal 50 PG™: 55.8% of phosphatidylcholine, 1.9% of soybean fatty acids, 2.9% of sunflower monoglycerides, 1.9% of ethanol, 37.3% of propylene glycol and 0.2% of ascorbyl palmitate;

NAT 8449™: 60% of phosphatidylcholine and 40% of propylene glycol

Phosal 53 MCT™: 60.8% of phosphatidylcholine, 2% of oleic acid, 3% of sunflower monoglycerides, 5% of ethanol, 29% of triglycerides and 0.2% of ascorbyl palmitate;

Phospholipon G-Na™: sodium salt of 3(3-sn-phosphatidyl)glycerol from soybean;

Phospholipon CC™: 1,2-dicaproyl-sn-glycero(3)phosphocholine;

Phospholipon SG-Na™: sodium salt of 1,2-distearoyl-sn-glycero(3)phosphoglycerol;

Phospholipon 90 H™: hydrogenated soybean (3-sn-phosphatidyl)choline.

EXAMPLE 1

This example illustrates the preparation of diverse compositions according to the invention. The compositions described below are in the form of more or less viscous emulsions, suspensions or solutions which gel instantaneously in the presence an aqueous phase.

General Procedure a:

Phosal 50 PG™ or NAT 8449™ and oleic acid are mixed with stirring. The active substance is introduced into the mixture with stirring. After homogenization, water is optionally added to make the preparation more viscous.

General Procedure b:

Phospal 50 PG™ or NAT 8449™ and oleic acid are mixed with stirring. The active substance is dissolved in water, and the solution thus obtained is introduced into the Phosal 50 PG™ or NAT 8449™/oleic acid mixture with stirring.

1.1. Preparation with Metronidazole Benzoate.

The preparations which have the compositions presented in Table 1 are obtained according to general procedure a.

TABLE 1

| Metronidazole Compositions A and B (parts) | | | | | |
|---|---|---|---|---|---|
| Composition | $A_1$ | $A_2$ | $A_3$ | $B_1$ | $B_2$ |
| Phosal 50 PG ™ | 54.6 | 77.4 | 81.9 | — | — |
| NAT 8449 ™ | — | — | — | 72.8 | 45.5 |
| Oleic acid | 36.4 | 13.6 | 9.1 | 18.2 | 45.5 |
| Metrodinazole benzoate | 5.0 | 5.0 | 5.0 | 5.0 | 5.0 |
| Water | 4.0 | 4.0 | 4.0 | 4.0 | 4.0 |

1.2 Preparation with Chlorhexidine Diacetate.

The preparations which have the compositions presented in Table 2 are obtained according to general procedure a.

TABLE 2

| Chlorhexidine Compositions C and D (parts) | | | | |
|---|---|---|---|---|
| Composition | $C_1$ | $C_2$ | $D_1$ | $D_2$ |
| Phosal 50 PG ™ | 51.0 | 63.8 | — | — |
| NAT 8449 ™ | — | — | 59.5 | 51.0 |
| Oleic acid | 34.0 | 21.2 | 25.5 | 34.0 |
| Chlorhexidine diacetate | 15.0 | 15.0 | 15.0 | 15.0 |

1.3. Preparation with Doxycycline Hyclate.

The preparations which have the compositions presented in Table 3 are obtained according to general procedure b.

TABLE 3

| Doxycycline Compositions E and F (parts) | | | | |
|---|---|---|---|---|
| Composition | $E_1$ | $E_2$ | $F_1$ | $F_2$ |
| Phosal 50 PG ™ | 43.0 | 64.5 | — | — |
| NAT 8449 ™ | — | — | 51.6 | 34.4 |
| Oleic acid | 43.0 | 21.5 | 34.4 | 51.6 |
| Doxycycline hyclate | 5.0 | 5.0 | 5.0 | 5.0 |
| Water | 9.0 | 9.0 | 9.0 | 9.0 |

1.4. Preparation with Minocycline Hydrochloride.

The preparations which have been compositions presented in Table 4 are obtained according to general procedure a.

TABLE 4

Minocycline Compositions G and H (parts)

| Composition | $G_1$ | $G_2$ | $H_1$ | $H_2$ |
| --- | --- | --- | --- | --- |
| Phosal 50 PG ™ | 45.5 | 77.4 | — | — |
| NAT 8449 ™ | — | — | 68.3 | 45.5 |
| Oleic acid | 45.5 | 13.6 | 22.7 | 45.5 |
| Minocycline hydrochloride | 5.0 | 5.0 | 5.0 | 5.0 |
| Water | 4.0 | 4.0 | 4.0 | 4.0 |

1.5. Preparation with 2,4-Dichlorobenzyl Alcohol

The preparations which have the compositions-presented in Table 5 are obtained according to general procedure a.

TABLE 5

2,4-Dichlorobenzyl alcohol Compositions I and J (parts)

| Composition | I | J |
| --- | --- | --- |
| Phosal 50 PG ™ | 80 | — |
| NAT 8449 ™ | — | 80 |
| Oleic acid | 19 | 19 |
| 2,4-Dichlorobenzyl alcohol | 1 | 1 |

1.6. Preparation with Hydrocortisone Succinate.

The preparations which have the compositions presented in Table 6 are obtained according to general procedure b.

TABLE 6

Hydrocortisone Compositions K and L (parts)

| Composition | K | L |
| --- | --- | --- |
| Phosal 50 PG ™ | 80 | — |
| NAT 8449 ™ | — | 67.0 |
| Oleic acid | 15 | 28.0 |
| Hydrocortisone succinate | 1 | 1 |
| Water | 4 | 4 |

1.7. Preparation with Lidocaine Hydrochloride.

The preparations which have the compositions presented in Table 7 are obtained according to general procedure b.

TABLE 7

Lidocaine Compositions M an N (parts)

| Composition | M | N |
| --- | --- | --- |
| Phosal 50 PG ™ | 80 | — |
| NAT 8449 ™ | — | 66 |
| Oleic acid | 14 | 28 |
| Lidocaine hydrochloride | 2 | 2 |
| Water | 4 | 4 |

1.8. Preparation with Somatostatin.

The preparations which have the compositions presented in Table 8 are obtained according to the following procedures: preparation $Z_1$: procedure a; preparations $Z_2$ to $Z_5$: procedure b.

EXAMPLE 2

Release Tests

Preparations $A_2$ and $B_1$ prepared in Example 1 were subjected to a release test carried out according to the standards in the 23rd edition of the U.S. pharmacopea (USP 23), using the machine No. 1 at a temperature of 37° C., with the paddles rotating at 50 rpm.

This test showed that preparation $A_2$ releases approximately 60% of the active principle in 6 hours, the release then continuing slowly to reach approximately 65% in 24 hours. With regard to preparation $B_1$, it releases approximately 45% of the active principle in 6 hours, and then the release continues slowly to reach approximately 55% in 24 hours.

2.2 The preparations $Z_1$ to $Z_5$ prepared in Example 1 were subjected to a release test which was carried out according to the standards of the 23rd edition of the U.S. pharmacopea (USP 23), using the machine No. 1 at a temperature of 37° C., with the paddles rotating at 50 rpm.

This test showed that preparation $Z_5$ releases approximately 23% of the active principle in 24 hours, the release continuing to reach approximately 31% in 48 hours; preparation $Z_3$ releases approximately 18% of the active principle in 24 hours; preparation $Z_1$ releases approximately 14% of the active principle in 24 hours; preparations $Z_2$ and $Z_4$ release approximately 7% of the active principle in 24 hours. These results show that it is possible to influence the release of the active principle by modifying the composition of the preparations.

EXAMPLE 3

This example shows that various pharmaceutically acceptable salts can be used in the compositions according to the present invention.

3.1. Composition O: Phospholipon $_{90}$™ (30 parts by weight) is dissolved while hot in polyethylene glycol 400 (45 parts by weight). After cooling, oleic acid is added with stirring. Upon contact with an aqueous solution, the preparation gels instantaneously.

This example shows that propylene glycol can be replaced with PEG 400.

3.2. Compositions P: 40.9 parts of NAT 8449™, 27.3 parts of PEG 400 and 22.8 parts by weight of oleic acid are mixed with stirring. Water (9 parts by weight) is added with stirring in order to make the preparation more viscous.

The preparations which have the compositions presented in Table 9 are obtained according to this procedure.

TABLE 9

Compositions P (parts)

| Composition | $P_1$ | $P_2$ | $P_3$ |
| --- | --- | --- | --- |
| NAT 8449 ™ | 34.1 | 40.9 | 61.4 |
| PEG 400 | 34.1 | 27.3 | 6.8 |
| Oleic acid | 22.8 | 22.8 | 22.8 |
| Water | 9.0 | 9.0 | 9.0 |

EXAMPLE 4

This example shows that the compositions according to the present; invention can also contain triglycerides.

Composition Q: 61.2 parts of Phosal 50 PG™, 20.4 parts of Phosal 53 MCT™ and 14.4 parts of oleic acid are mixed with stirring. 4 parts of water are then added to this mixture with stirring.

This preparation gels instantaneously upon contact with an aqueous phase.

EXAMPLE 5

This example shows that the compositions according to the present invention can contain various types of phospholipid. The phospholipids used are the sodium salt of 3-(3-sn-phosphatidyl)glycerol from soybean (Phospholipon G-Na™), 1,2-dicaproyl-sn-glycero(3)phosphocholine (Phospholipon CC™), the sodium salt of 1,2-distearoyl-sn-glycero(3)phosphoglycerol (Phospholipon SG-Na™) and hydrogenated soybean (3-sn-phosphatidyl)choline (Phospholipon 90H™).

The compositions P presented in Table 10 are obtained by mixing the various components with stirring. These four compositions gel instantaneously in the presence of an aqueous phase.

TABLE 10

Compositions R (parts)

| Composition | $R_1$ | $R_2$ | $R_3$ | $R_4$ |
|---|---|---|---|---|
| Phospholipon G-Na ™ | 30 | — | — | — |
| Phospholipon CC ™ | — | 30 | — | — |
| Phospholipon SG-Na ™ | — | — | 15 | — |
| Phospholipon 90H ™ | — | — | — | 3 |
| PEG 400 | 45 | 45 | 60 | 72 |
| Oleic acid | 25 | 25 | 25 | 25 |

EXAMPLE 6

This example shows that oleic acid can be replaced with other fatty acids or with a fatty alcohol in the compositions according to the present invention.

The Compositions S presented in Table 11 are obtained by mixing the various components with stirring. These four compositions gel instantaneously in the presence of an aqueous phase.

TABLE 11

Compositions S (parts)

| Composition | $S_1$ | $S_2$ | $S_3$ | $S_4$ |
|---|---|---|---|---|
| Phosal 50PG ™ | 80 | 80 | 80 | 80 |
| Caprylic acid | 20 | — | — | — |
| Capric acid | — | 20 | — | — |
| Oleic acid | — | — | 20 | — |
| Oleyl alcohol | — | — | — | 20 |

EXAMPLE 7

Measurement of the Rate of Release as a Function of the Excipients

7.1. The Compositions T presented in Table 12 are obtained by adding the desired amount of an aqueous solution containing 10% of Sicomet-FDC blue 1 dye to the mixture of the other components, with stirring. Compositions $T_1$ to $T_6$ gel instantaneously in the presence of an aqueous phase; the gel is more fluid for the composition $T_7$.

TABLE 12

Compositions T (parts)

| Composition | Control | $T_1$ | $T_2$ | $T_3$ | $T_4$ | $T_5$ | $T_6$ | $T_7$ |
|---|---|---|---|---|---|---|---|---|
| Phosal 50 PG ™ | — | 81.6 | 68.3 | 68.3 | 68.3 | 68.3 | 68.3 | 40.8 |
| Oleic acid | — | 14.4 | 22.7 | 18.2 | 13.7 | 18.2 | 9.0 | 14.4 |

TABLE 12-continued

Compositions T (parts)

| Composition | Control | $T_1$ | $T_2$ | $T_3$ | $T_4$ | $T_5$ | $T_6$ | $T_7$ |
|---|---|---|---|---|---|---|---|---|
| Miglyol 810N ™ | — | — | — | 4.5 | 9.0 | — | 13.7 | — |
| Phosal 53 MCT ™ | — | — | — | — | — | 4.5 | — | 40.8 |
| Dye solution | 100 | 4.0 | 9.0 | 9.0 | 9.0 | 9.0 | 9.0 | 4.0 |

The release test is carried out as follows. Equal amounts of preparations $T_1$ to $T_7$ and of the control solution are placed in a well which is hollowed out at the center of a layer of trypticase soy agar which has a constant thickness and which has been poured in a Petri dish. The rate of diffusion of the dye is determined by measuring the diameter of the dye stain as a function of time. The results obtained for the control solution and the solutions $T_1$ to $T_7$ are given in Table 13.

TABLE 13

Rate of release of preparations $T_1$ to $T_7$. Diameter of the stain in mm.

| Time (hours) | Control | $T_1$ | $T_2$ | $T_3$ | $T_4$ | $T_5$ | $T_6, T_7$ |
|---|---|---|---|---|---|---|---|
| 0 | 16.97 | 18.74 | 18.61 | 17.66 | 18.36 | 18.49 | * |
| 3 | 49.55 | — | — | — | — | — | * |
| 6 | 62.18 | 29.56 | 29.14 | 28.58 | 23.12 | 33.33 | * |
| 24 | 90.10 | 51.00 | 30.38 | 30.57 | 24.59 | 52.96 | * |
| 36 | 96.29 | 57.45 | 34.02 | 33.67 | 31.23 | 54.55 | * |
| 72 | 108.52 | 60.45 | 39.29 | 34.58 | 31.82 | 68.67 | * |

*No diffusion is observed.

This example shows that the rate of release of an active substance can be controlled through the choice of the components of the preparation.

7.2. Similarly, the Compositions U given in Table 14 were prepared.

TABLE 14

Compositions U (parts)

| Composition | $U_1$ | $U_2$ | $U_3$ | $U_4$ |
|---|---|---|---|---|
| Phosal 50PG ™ | 81.6 | 86.4 | 91.2 | 91.2 |
| Oleic acid | 14.4 | 9.6 | 4.8 | 4.8 |
| Dye solution | 4.0 | 4.0 | 4.0 | 4.0 |

A release test as described in Example 7.1 is carried out on compositions U1 to U4; for comparison, a release test is simultaneously carried out with the solution T7 and with a solution containing 10% of Sicomet-FDC blue 1 (control). The results of this test are presented in Table 15.

TABLE 15

Rate of release of preparations $U_1$ to $U_4$ and $T_7$.

| Time (hours) | control | $U_1$ | $U_2$ | $U_3$ | $U_4$ | $T_7$ |
|---|---|---|---|---|---|---|
| 2 | 46 | 18 | 24 | 27 | 24 | 18 |
| 4 | 55 | 18 | 28 | 34 | 26 | 18 |

TABLE 15-continued

Rate of release of preparations $U_1$ to $U_4$ and $T_7$.

| Time | Diameter of the stain in mm. | | | | | |
|---|---|---|---|---|---|---|
| (hours) | control | $U_1$ | $U_2$ | $U_3$ | $U_4$ | $T_7$ |
| 6 | 62 | 18 | 33 | 40 | 28 | 18 |
| 24 | 82 | 23 | 48 | 47 | 37 | 18 |

These results show that the rate of release of an active substance can be controlled by the choice of the components of the preparation.

EXAMPLE 8

In Vivo Trials
Subcutaneous and Intramuscular Injection of a Preparation with Calcitonin.

Calcitonin causes a decrease in the serum calcium level which is directly related to its activity. During these trials, the evolution over the course of time of the serum calcium level in rats was followed after subcutaneous or intramuscular injection of preparations according to the invention containing 20 IU of salmon calcitonin.

8.1 Formulations.

The compositions comprising salmon calcitonin which were used in these trials are given in Table 16.

TABLE 16

| | Compositions X (parts) | | |
|---|---|---|---|
| Composition | $X_1$ | $X_2$ | $X_3$ |
| Phosal 50PG ™ | — | 40.8 | 81.6 |
| Phosal 53 MCT ™ | — | 40.8 | — |
| Oleic acid | — | 14.4 | 14.4 |
| Calcitonin | 10,000 IU | 10,000 IU | 10,000 IU |
| Acetic buffer pH 4.3 | 100 | 4.0 | 4.0 |

The calcitonin used contains 5660 IU/mg. The 10,000 IU present in preparations $X_1$ to $X_3$ correspond to 1.767 mg.

8.2. Animal Experiments.

The experiments concerned two groups of 18 non-fasted conscious male Wistar rats (originating from IFFA CREDO) weighing from 169.1 g to 193.6 g (mean: 183.0 g; standard error: 5.9 g), for the first group, and weighing from 170.2 g to 189.1 g (mean: 180.0 g; standard error: 5.2 g), for the second group. Each group of 18 animals is divided into 3 series of 6:

First group:
  Series 1: each rat receives 200 µl of the preparation $X_1$, i.e. 20 IU of calcitonin, subcutaneously in the abdominal region;
  Series 2: each rat receives 200 µl of the preparation $X_2$, i.e. 20 IU of calcitonin, subcutaneously in the abdominal region;
  Series 3: each rat receives 200 µl of the preparation $X_2$, i.e. 20 IU of calcitonin, subcutaneously in the abdominal region. Second group:
  Series 4: each rat receives 200 µl of the preparation $X_1$, i.e. 20 IU of calcitonin, intramuscularly in the thigh muscle;
  Series 5: each rat receives 200 µl of the preparation $X_2$, i.e. 20 IU of calcitonin, intramuscularly in the thigh muscle;
  Series 6: each rat receives 200 µl of the preparation $X_2$, i.e. 20 IU of calcitonin, intramuscularly in the thigh muscle.

After administration of the preparations, the rats receive a food which is low in calcium and deionized water.

300 µL blood samples are taken from the tail vein before administration (t=0) and at the following times after administration: 30 min, 1 h, 2 h, 4 h, 8 h, 24 h, 32 h and 48 h. The samples are left to stand for 1 h at room temperature before undergoing 2 successive centrifugations at 6000 rpm for 10 minutes. The sera harvested are frozen at −20° C. until the time of the serum calcium assay.

8.3. Serum Calcium Assay.

A 90 µL serum sample is added to 2 mL a solution of lanthanum chloride (15 mmol/L) in hydrochloric acid (50 mmol/L). The calcium level of the sample thus diluted is measured using an atomic absorption spectrophotometer (Varian Spectra A-40) (extinction at 422.7 nm). The standard curve is produced at the start from 5 standard solutions:

a blank containing sodium chloride (140 mmol/L), potassium chloride (5 mmol/L), hydrochloric acid (30 mmol/L) and magnesium acetate (1 mmol/L)

the standard solutions containing, in addition to the blank, calcium carbonate at the concentrations of 1.25/2.5/5 and 7.5 mmol/L.

The machine is calibrated before each series of rats. The calcium level of the samples is calculated from the standard curve (Data Station Varian). The calculated concentrations are then expressed as a percentage of the initial value, i.e. the value obtained before any treatment (t=0). These initial values vary according to the animal from 3.34 to 2.26 mmol/L.

The results obtained with the series 1, 2 and 3 (subcutaneous administration) are presented in Table 17, which gives the means of the serum calcium levels, expressed as a percentage of the initial concentration (t=0), and the standard errors of these means obtained for the preparations $X_1$, $X_2$ and $X_3$.

TABLE 17

Serum calcium levels ± standard error as a function of time after subcutaneous injection of the formulations $X_1$, $X_2$ and $X_3$.

| Time (h) | $X_1$ | $X_2$ | $X_3$ |
|---|---|---|---|
| 0 | 100 | 100 | 100 |
| 0.5 | 86.52 ± 2.90 | 91.11 ± 1.59 | 90.72 ± 2.17 |
| 1 | 80.33 ± 4.29 | 84.00 ± 2.05 | 86.59 ± 2.39 |
| 2 | 69.13 ± 1.79 | 74.43 ± 2.38 | 75.69 ± 1.62 |
| 4 | 59.26 ± 0.86 | 73.62 ± 4.41 | 69.19 ± 2.39 |
| 8 | 55.04 ± 1.12 | 82.30 ± 7.26 | 66.52 ± 1.13 |
| 24 | 97.14 ± 2.38 | 95.65 ± 3.93 | 73.38 ± 3.59 |
| 32 | 101.03 ± 2.99 | 93.85 ± 3.90 | 75.98 ± 2.40 |
| 48 | 97.32 ± 3.44 | 100.09 ± 1.75 | 87.13 ± 1.51 |

The results obtained with the series 4, 5 and 6 (intramuscular administration) are presented in Table 18, which gives the means of the serum calcium levels, expressed as a percentage of the initial concentration (t=0), and the standard errors of these means obtained for the preparations $X_1$, $X_2$ and $X_3$.

TABLE 18

Serum calcium levels ± standard error as a function of time after intramuscular injection of the formulations $X_1$, $X_2$ and $X_3$.

| Time (h) | $X_1$ | $X_2$ | $X_3$ |
|---|---|---|---|
| 0 | 100 | 100 | 100 |
| 0.5 | 86.51 ± 2.09 | 89.06 ± 1.39 | 88.27 ± 1.64 |
| 2 | 78.77 ± 1.80 | 79.31 ± 1.55 | 81.81 ± 1.86 |
| 2 | 73.89 ± 1.82 | 75.82 ± 2.52 | 75.95 ± 1.31 |
| 4 | 65.63 ± 1.32 | 68.58 ± 2.14 | 72.74 ± 1.57 |
| -8 | 62.93 ± 1.55 | 63.91 ± 1.45 | 66.01 ± 1.55 |
| 24 | 83.70 ± 3.25 | 78.66 ± 4.07 | 74.12 ± 2.38 |
| 32 | 94.50 ± 1.70 | 85.83 ± 4.41 | 78.12 ± 2.24 |
| 48 | 98.53 ± 2.76 | 105.33 ± 4.15 | 100.62 ± 1.34 |

These results show a prolongation of the effect of calcitonin, after subcutaneous or intramuscular administration, of several hours for the preparations $X_2$ and $X_3$ with respect to the effect of the reference solution $X_1$, this effect being greater for the preparation $X_3$ than for the preparation $x_2$.

These assays also show that it is possible to modify, in vivo, the biological activity of the active principle by modifying the composition of the preparations. This is clearly apparent in Table 19, which gives the relative bioavailabilities (with respect to the solution $X_1$) of the preparations $X_2$ and $X_3$ after subcutaneous (s.c.) and intramuscular (i.m.) injections.

TABLE 19

Relative bioavailability (%) of the preparations $X_2$ and $X_3$.

| Injection | $X_2$ | $X_3$ |
|---|---|---|
| Subcutaneous | 63.89 | 172.56 |
| Intramuscular | 110.41 | 128.72 |

What is claimed is:

1. Fluid pharmaceutical composition which allows the controlled release of at least one active substance and which comprises
   a) a therapeutically effective amount of at least one active substance,
   b) from 3 to 55% by weight of phospholipid,
   c) from 16 to 72% by weight of pharmaceutically acceptable solvent, and
   d) from 4 to 52% by weight of fatty acid,
said composition having the property of gelling instantaneously in the presence of an aqueous phase.

2. Pharmaceutical composition according to claim 1, wherein the active substance is chosen from antibiotics, anti-infectious agents, local anesthetics, anti-inflammatory agents, anti-mycotic agents and peptide active substances.

3. Pharmaceutical composition according to claim 1, wherein the phospholipid is chosen from phosphatidylcholine, phosphatidylglycerol salts, dicaproylphosphatidylcholine and distearoylphosphatidylglycerol salts, alone or as a mixture.

4. Pharmaceutical composition according to claim 3, wherein it contains from 15 to 55% by weight of phospholipid.

5. Pharmaceutical composition according to claim 1, wherein the phospholipid is a hydrogenated phosphatidylcholine.

6. Pharmaceutical composition according to claim 5, wherein it contains from 3 to 11% by weight of phospholipid.

7. Pharmaceutical composition according to claim 1, wherein the pharmaceutically acceptable solvent is chosen from propylene glycol, polyethylene glycols and mineral oils alone or as a mixture.

8. Pharmaceutical composition according to claim 1, wherein the fatty acids used are saturated or unsaturated organic carboxylic acids containing from 4 to 22 carbon atoms.

9. Pharmaceutical composition according to claim 8, wherein the fatty acids are chosen from oleic acid, caprylic acid, capric acid, caproic acid, myristic acid and butyric acid, alone or as a mixture.

10. Pharmaceutical composition according to claim 1, wherein it also comprises up to 5% by weight of monoglyceride or of diglyceride or of a mixture of mono- and of diglyceride, and/or up to 15% by weight of triglycerides.

11. Method for manufacturing a pharmaceutical composition according to claim 1, which comprises the following successive steps:
   i) the phospholipid(s) is(are) dissolved in the pharmaceutically acceptable solvent;
   ii) the fatty acid(s) is(are) added to the phospholipid solution with stirring;
   iii) the active substance(s) is(are) incorporated into the mixture obtained at the end of step ii), and
   iv) water is optionally added to the composition obtained in step iii).

12. Method according to claim 11, wherein the active substance(s) is(are) dissolved in a minimum amount of water before the incorporation in step iii).

13. Method according to claim 11, wherein the active substance(s) is(are) incorporated in step iii), optionally in micronized form.

14. A method for providing a controlled release of a pharmaceutical composition according to claim 1, which comprises administering to a patient in need thereof, the pharmaceutical composition according to claim 1 by subcutaneous and/or intramuscular injection.

15. Pharmaceutical composition according to claim 3, wherein it contains from 15 to 51% by weight of phospholipid.

16. Pharmaceutical composition according to claim 5, wherein it contains from 3 to 10% by weight of phospholipid.

17. Pharmaceutical composition according to claim 1, wherein the fatty acids used are saturated or unsaturated organic carboxylic acids containing from 8 to 18 carbon atoms.

18. Pharmaceutical composition according to claim 7, wherein the mineral oils are selected from the group consisting of liquid paraffin and silicone oils.

* * * * *